United States Patent [19]

Gramkow et al.

[11] Patent Number: 5,439,644
[45] Date of Patent: Aug. 8, 1995

[54] APPARATUS FOR THE REGISTRATION OF THE CONTENTS OF HUMIDITY AND ACID IN A COOLANT

[75] Inventors: Asger Gramkow, Gammelgard 27, DK-6440 Augustenborg; Jeppe C. Bastholm, Sonderborg, both of Denmark

[73] Assignee: Asger Gramkow, Augustenborg, Denmark

[21] Appl. No.: 162,197

[22] PCT Filed: Jun. 17, 1992

[86] PCT No.: PCT/DK92/00109
§ 371 Date: Jan. 19, 1994
§ 102(e) Date: Jan. 19, 1994

[87] PCT Pub. No.: WO92/22809
PCT Pub. Date: Dec. 23, 1992

[30] Foreign Application Priority Data
Jun. 18, 1991 [DK] Denmark ............... 1184/91

[51] Int. Cl.⁶ ........................... G01N 27/10
[52] U.S. Cl. ............... 422/62; 422/82.02; 324/442; 324/444
[58] Field of Search .......... 422/82.02, 82.01, 62; 436/39, 100, 150, 151; 324/438, 439, 442, 444; 204/406

[56] References Cited

U.S. PATENT DOCUMENTS

| | | | |
|---|---|---|---|
| 4,890,459 | 1/1990 | Havemann | 62/126 |
| 4,923,806 | 5/1990 | Klodowski | 436/39 |
| 5,071,768 | 12/1991 | Klodowski | 436/39 |
| 5,235,267 | 8/1993 | Schoneberg et al. | 422/82.02 X |
| 5,289,132 | 2/1994 | Oksman et al. | 422/82.02 X |

FOREIGN PATENT DOCUMENTS

| | | |
|---|---|---|
| 370801 | 10/1974 | Sweden. |
| 2045442 | 10/1980 | United Kingdom. |
| 2149117 | 6/1985 | United Kingdom. |

*Primary Examiner*—Jeffrey R Snay
*Attorney, Agent, or Firm*—Watson, Cole, Grindle & Watson

[57] ABSTRACT

An apparatus for the registration of the humidity and acid content of a refrigerant or another non-polar liquid including a capacitive sensing element placed in the refrigerant or liquid and connected to an electrical evaluation circuit, the electrodes of the capacitive sensing element being formed of two different metals having different normal potentials, and the electrical circuit includes circuit elements for determining the resistive loss in the capacitive sensing element and circuit breakers for determining the current delivered by the sensing element.

9 Claims, 5 Drawing Sheets

APPARATUS FOR THE REGISTRATION OF THE CONTENTS OF HUMIDITY AND ACID IN A COOLANT

BACKGROUND OF THE INVENTION

1. Field of the Invention

The present invention relates to an apparatus for the registration or measurement of the humidity and acid content of a refrigerant including a capacitive sensing element for placing in contact with the refrigerant, the sensing element having electrodes consisting of two different metals with different normal potentials, and in which apparatus the determination of humidity is carried out by measuring a resistive loss in the sensing element.

2. The Prior Art

In refrigerants, such as freon, CFC, R12, R22, R502, R134a, etc., used in refrigeration and air conditioning circuits, an undesired concentration of not only humidity but also acid may occur or develop. If there is a considerable concentration of humidity, the humidity will directly prevent the refrigeration circuit from functioning, as the valves and the capillary tubes are blocked by ice formed at the low temperatures. If there is a considerable acid content, the acid will have a detrimental effect on the components of the refrigeration circuit, such as compressor, etc.

The increasing awareness of the damaging effect of some refrigerants on the ozone layer in the atmosphere has made purification (recycling) of used refrigerant desirable, and in some countries it has been made compulsary by law. Using this purification it is desired to remove i.a. water and acid in order to raise the refrigerant to the standard applying to new refrigerant.

Consequently, there is a need for effecting a registration, monitoring or measurement of the humidity and acid content of refrigerants in order to prevent the above-mentioned detriment or blocking of the refrigeration circuit or to make sure that the requirements stipulated as to the purity of the refrigerant are complied with when purifying the refrigerant.

It is known to monitor the humidity content of refrigeration circuits by means of a humidity indicator consisting of a housing with a sight glass and some crystals placed under this sight glass. These crystals turn from yellow to green, dependent on the humidity content of the refrigerant. This change of colour can be observed through the sight glass and is an expression of the humidity content. The method is well known and sturdy but very unreliable and quite unsuitable in connection with the purification of refrigerants, as a maximum humidity level of, e.g., 10–15 ppm, cannot be registered at temperatures above 30° C., due to the temperature dependency of the crystals.

For the registration of the acid content of refrigeration circuits a method is known, in which a sample of the compressor liquid is taken and subsequently the pH-value thereof is controlled by a simple litmus test. A method of testing both the humidity and the acid content by means of "Dräger tubes" is also known. This method is chemical and in this case a change of colour occurs as an expression of a change in the concentration of humidity and acid.

The two latter methods cannot be used for continuous monitoring, and besides they are inconvenient and unreliable.

Furthermore, laboratory methods are known which use gas chromatography and mass spectrometry, but these methods are self-evidently very cost demanding and irrelevant in the present connection.

Apparatuses of the type mentioned above, but which are merely designed for measuring the humidity content of liquids, air or solid materials, such as grain, are disclosed in e.g. GB patent applications Nos. 2,149,117 A, and 2,045,442 A and in DK published patent application No. 129,603. The impedance of the capacitive sensing element varies, dependent on the humidity content of the material with which the sensing element is in contact, and is measured or registered by the electrical circuit which may assume different forms to deliver an electric output signal or to effect a regulation, dependent on the measured humidity.

SE patent No. 370,801 discloses an apparatus for measuring humidity wherein two electodes of different materials with different normal potentials are fed by a D.C. voltage source and are connected to a detector for sensing the potential difference between the electrodes. The indicator is in the form of a differential amplifier, which, e.g., may be coupled in such a manner that different D.C. voltage levels are delivered on its output, dependent on whether there is humidity between the electrodes or not, or whether the electrodes are short-circuited. This prior art apparatus is designed merely to indicate the humidity condition between the electrodes.

SUMMARY OF THE INVENTION

The object of the present invention is to remedy the drawbacks of the prior art methods and to provide an apparatus in which both the humidity and the acid content of refrigerants can be registered or monitored continuously during their use in refrigeration circuits or during purification (recycling), and according to the present invention this is obtained with an apparatus of the type stated above, which apparatus is characterized in that the capacitive sensing element is connected to an A.C. voltage source and the sensing element is connected to an electrical circuit comprising means for converting the resistive A.C. loss in the capacitive sensing element to an absolute D.C. voltage when measuring humidity, and means for determining the absolute D.C. current delivered by the sensing element when measuring acid.

Thus, a measurement of both the humidity and acid content of the refrigerant can be effected simultaneously and independently in a simple manner and by use of one and the same capacitive sensing element, as the galvanic element formed by the capacitive sensing element in the presence of acid will deliver a D.C. current at constant voltage determined by the metals forming part of the element, the amount of which D.C. current depends on the concentration of acid and is zero in the absence of acid in the refrigerant. The resistive A.C. loss in the capacitive sensing element in the presence of water can be measured independently thereof by means of the A.C. current.

In an advantageous embodiment of the apparatus according to the invention the circuit means for determining the resistive loss in the capacitive sensing element comprises an integrator, of which the capacitive sensing element forms part, a phase synchronous rectifier connected to the integrator and a humidity detector circuit connected to the rectifier. The phase synchronous rectification of the output signal of the integrator ensures that a D.C. voltage, if any, formed in the sensing element does not affect the humidity measurement.

The invention will be explained in further detail below with reference to the drawings

DETAILED DESCRIPTION OF THE PREFERRED EMBODIMENT

Figure 1:
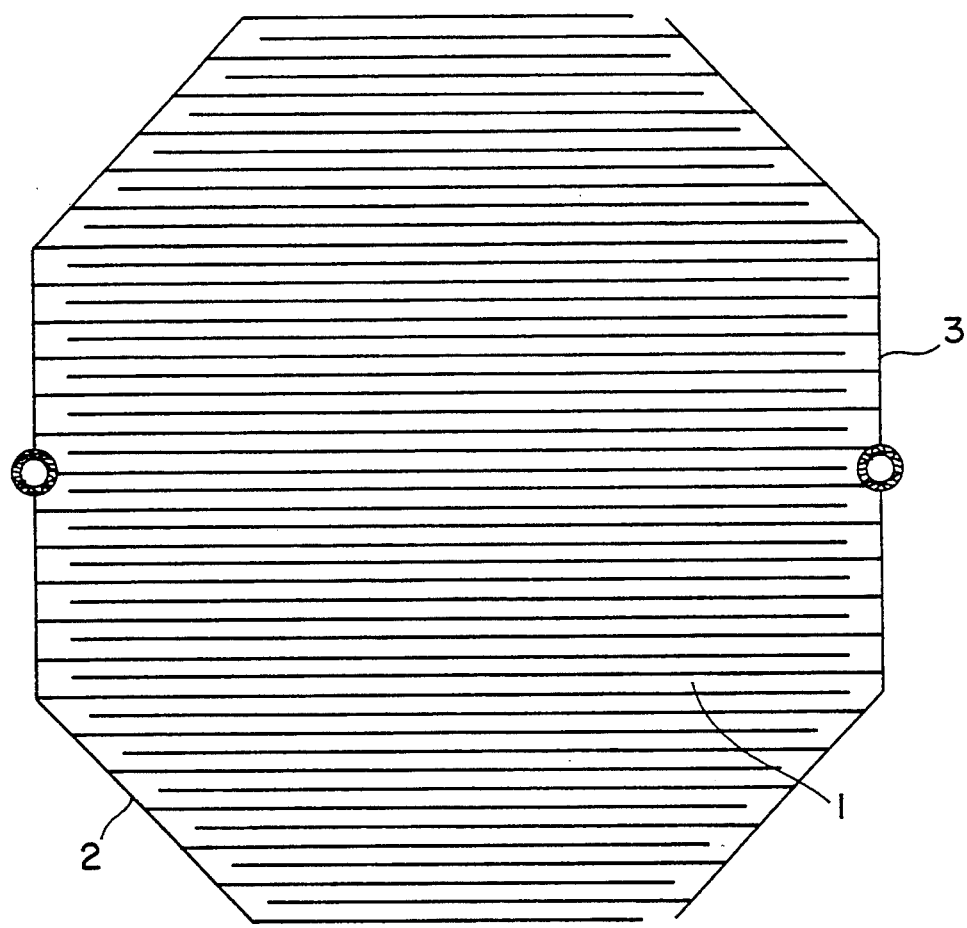
FIG. 1 shows an embodiment of a measurement capacitor according to the invention.

FIG. 1 in the drawing shows a measurement capacitor 1 consisting of two electrodes or measurement capacitor plates 2 and 3 designed as two mutually engaging cams of two different metals with different normal potentials, e.g. Cu and A1 or Ni. The measurement capacitor 1 is expediently made on a conventional printed circuit board, as Cu is removed by etching on parts of the surface of the board and A1, Ni, etc., are applied thereon. In the drawing the measurement capacitor 1 has an octagonal form to fit with approximation in a tubular element in which the refrigerant/liquid flows, but of course other forms are also possible.

Figure 2:
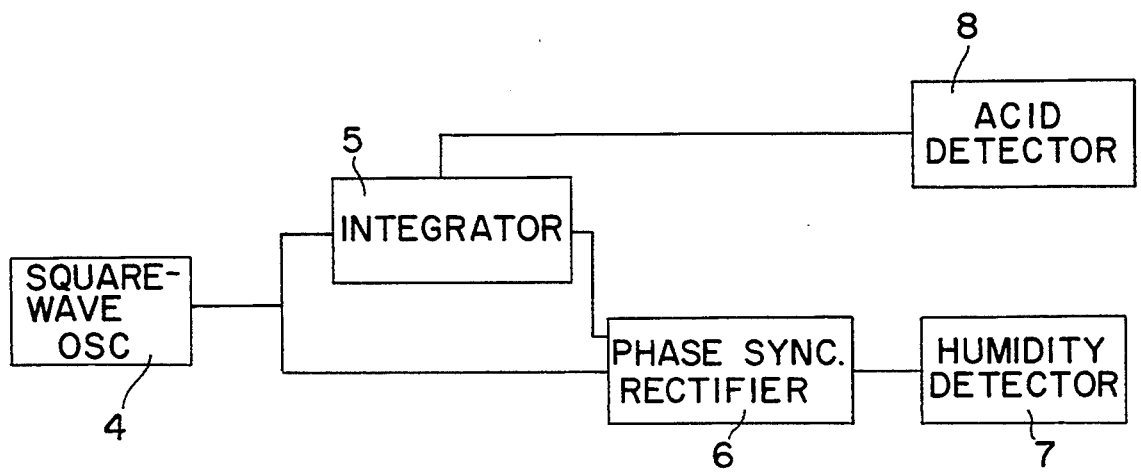
FIG. 2 is a block diagram of a measuring circuit according to the invention.
Figure 3:
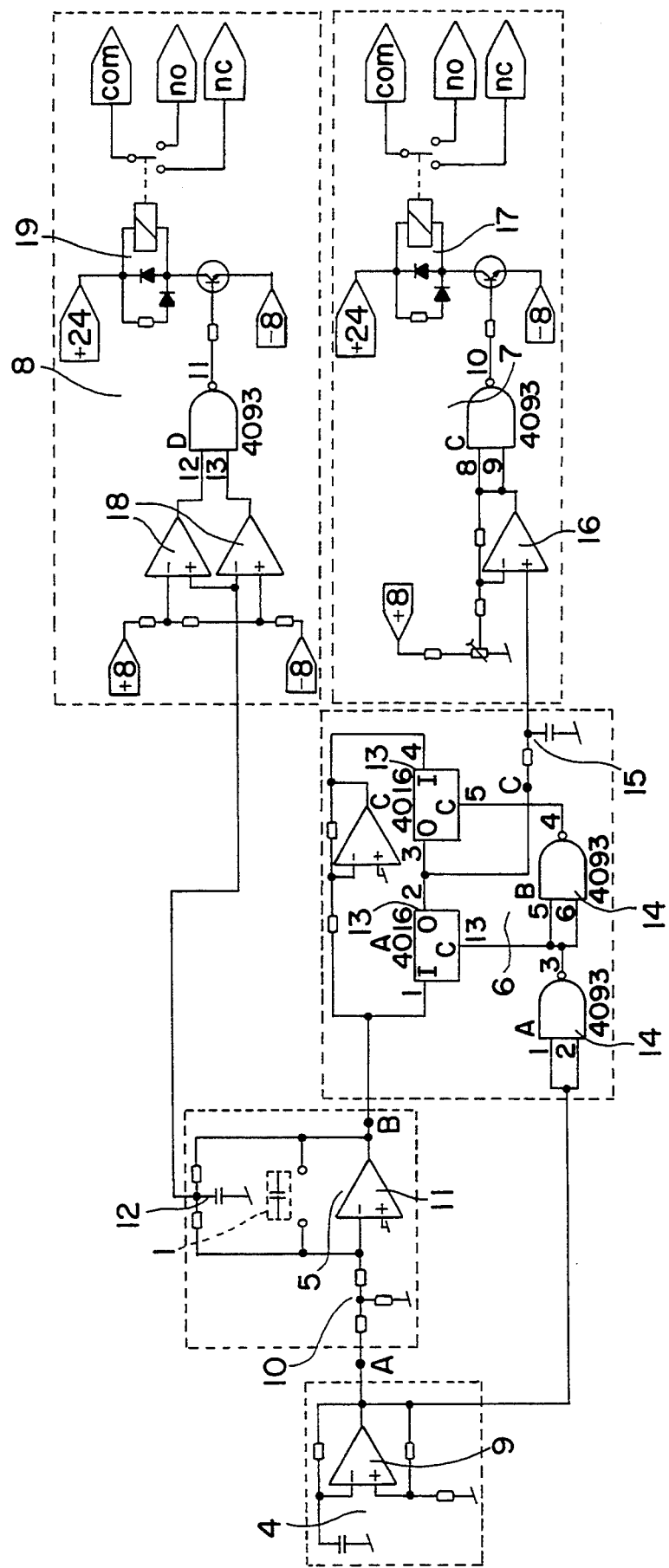
FIG. 3 is a more detailed diagram of the measuring circuit of FIG. 2, FIGS. 4a-4d are curves of the signal course at the output of an integrator forming part of the circuit of FIG. 3, FIGS. 5a-5e are curves of the signal course at three different points in the circuit of FIG. 3, and FIG. 6 a further curve of the signal course after a phase synchronous rectifier forming part of the circuit of FIG. 3.
Figure 4A:
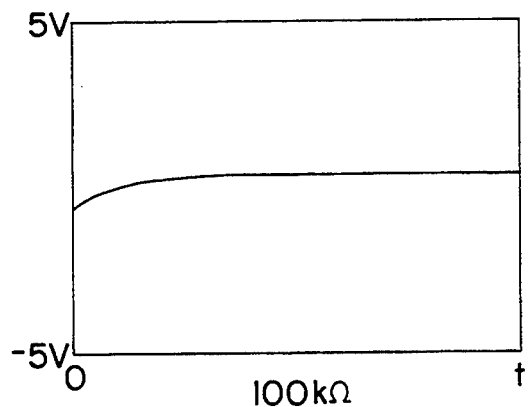
Figure 4B:
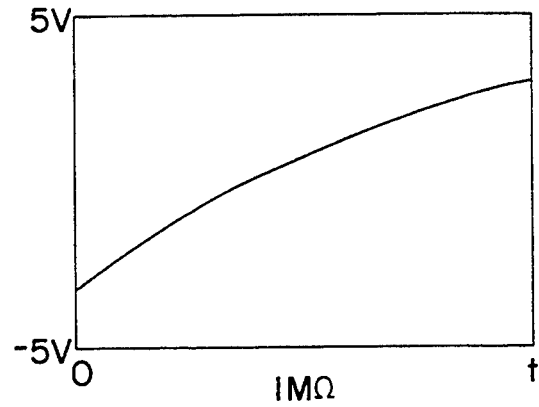
Figure 4C:
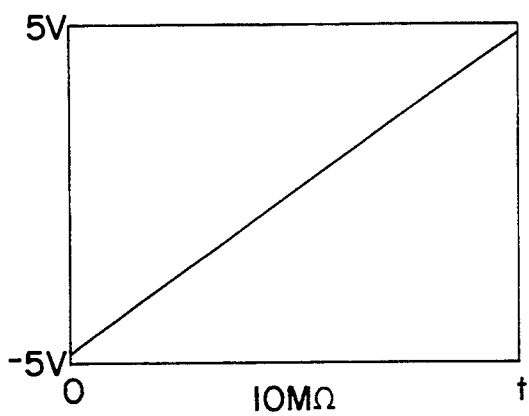
Figure 4D:
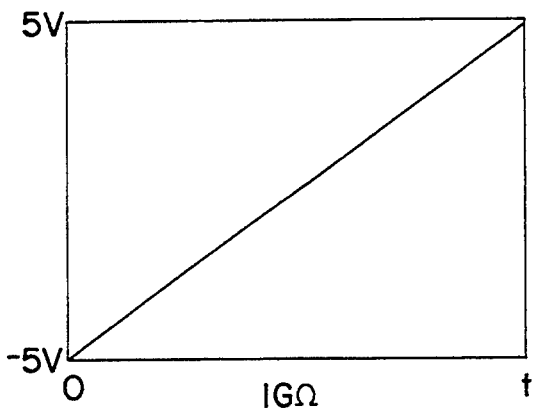

In FIGS. 2 and 3, 4 shows a square-wave oscillator consisting of an operational amplifier 9 with associated coupling resistors. The oscillator is designed so that it oscillates symmetrically with respect to both voltage and time at a frequency which may be selected e.g., from 10 to 100 kHz.

Figure 5A:
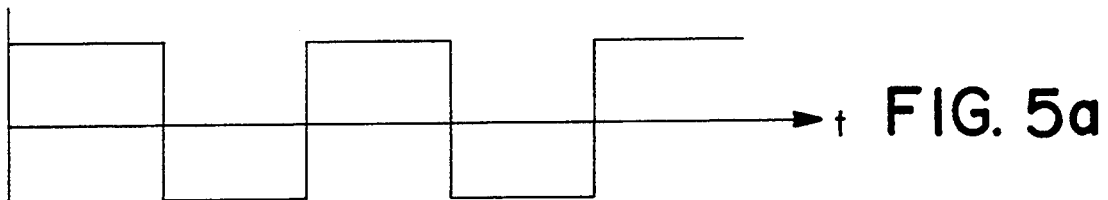

The signal occurring at point A at the output of the oscillator 4 is shown in FIG. 5a. This square-wave signal is delivered to an integrator 5 via a voltage divider 10 in order to adapt the current to the operational amplifier 11 of the integrator. Between the output and one of the inputs of the operational amplifier the measurement capacitor 1 is interposed as well as a D.C. feedback element 12 in the form of a voltage divider which i.a. serves to maintain the D.C. stability of the integrator, as the output signal otherwise may be completely indefinite.

Figure 5B:
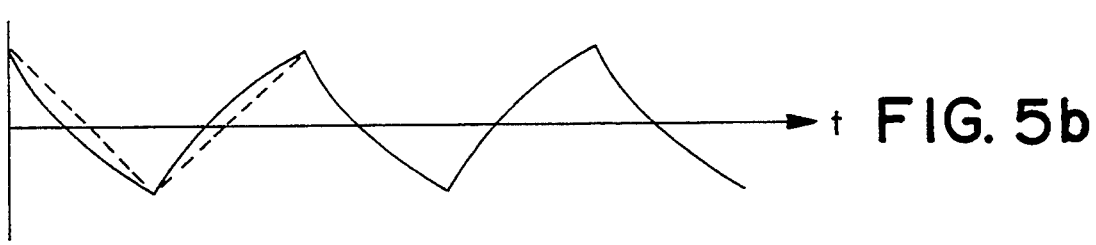

FIG. 5b shows the signal at the output of the integrator, and as will appear the square-wave voltage has been converted to a symmetrically oscillating triangular voltage, i.e., it is symmetrical about zero voltage, and this applies irrespective of whether there is a great or small resistive loss in the measurement capacitor 1. It also applies irrespective of a change in the capacity proper of the measurement capacitor 1.

Figure 5C:
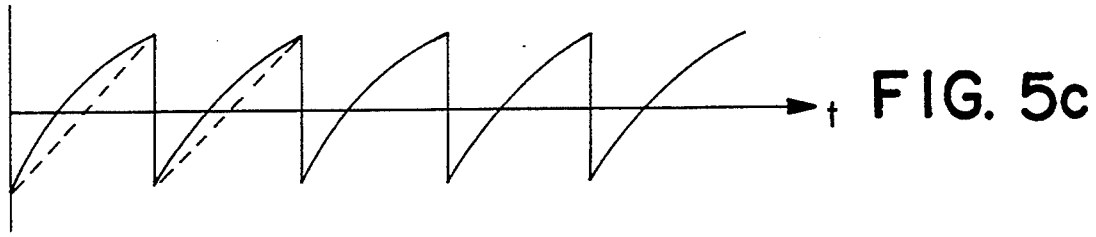

The output signal of the integrator is delivered to a phase synchronous rectifier 6 consisting of two analog switches 13 which are controlled by the square-wave signal of the oscillator 4 by means of two NAND gates 14. FIG. 5c shows the output signal of the rectifier at C. This signal is delivered across a RC-coupling 15 to one o; the inputs of an operational amplifier 16 in a humidity detector 7 which at its output is provided with a relay 17 which is tripped when the output signal exceeds a pre-determined level of a voltage, which is a representation of the humidity content. Instead of a relay an analog indicator or display device, for example, may be connected to the detector output. In order to ensure a correct detection hysteresis is expediently embedded in the humidity detector 7.

As the measurement capacitor 1 is made of two different metals with different normal potentials, the plates 2 and 3 of the measurement capacitor will serve as electrodes in a galvanic element in the presence of acid and give rise to a current which depends on the acid-ion-concentration. However, the generated D.C. voltage is constant and solely determined by the two metals used in the measurement capacitor/element.

The current produced by the element causes a shift of the D.C. voltage working point of the integrator 5. However, this does not affect the measurement of humidity, as the voltage at B at the integrator output is phase synchronously rectified in the circuit 6 so that this D.C. voltage will provide the amount of zero volt.

The D.C. voltage on the integrator 5 allows the signal which is dependent on the acid-ion concentration to be derived from the above mentioned D.C. feedback circuit 12 of the integrator. The derived voltage signal is delivered to two comparator circuits 18 in an acid detector 8 which at its output is provided with a relay 19 which is tripped when the output signal exceeds a pre-determined level. As is the case with the humidity detector, an analog indicator or display device, for example, may of course also be connected to the output of the acid detector instead of the relay.

It should be noted that FIGS. 5b and 5c show the signals at the respective points in the circuit, when no acid is present in the refrigerant with which the measurement capacitor 1 is in contact.

Figure 5D:
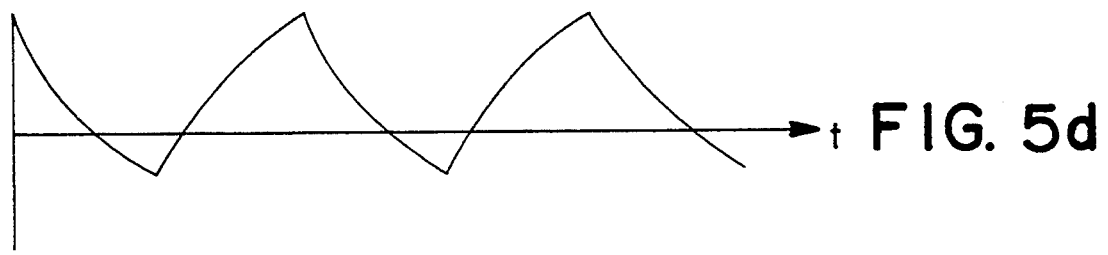
Figure 5E:
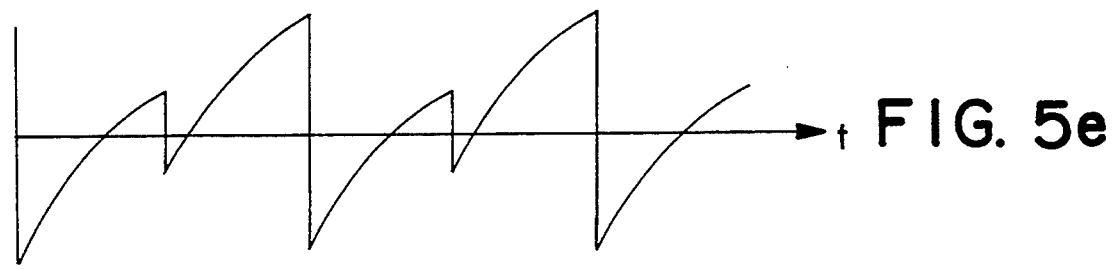

In case of an acid content in the refrigerant, the curve course at point B will be displaced as indicated in FIG. 5d, and after the phase synchronous rectification the curve will have the course indicated by in FIG. 5e.

The registration of humidity in the refrigerant is based on a change in the curve form of the above-mentioned triangular wave voltage formed by the integrator 5, as this voltage changes from rectilinear, as indicated by the dotted line in FIG. 5b and 5c in the absence of humidity, to curved in the presence of humidity. This curvature is registered in the phase synchronous rectifier 6 which also carries out an electrical integration of the curvature which is proportional to the humidity content.

As will immediately appear from FIG. 5c, the size of the areas above and below the zero line is equal in the absence of humidity but in the presence of humidity the curvature of the curve reduces the area below the zero line and increases the area above the zero line, thereby resulting in a continuously higher integration value the more the curve bends, i.e., the higher the humidity content.

FIGS. 4a-4d of the drawings shows curve forms of the signal at point B immediately after the integrator 5 at four different resistive losses in the measurement capacitor 1 expressed by equivalent loss resistances of 100 kohm, 1 Mohm, 10 Mohm and 1 Gohm. As will appear, the voltage decreases substantially linearly at resistances of, e.g., 10 Mohm and higher. At 1 Mohm, a certain curvature of the curve is observed because the measurement capacitor absorbs energy during the charging operation and consequently the voltage across the measurement capacitor increases more slowly. At the same time, the zero point is shifted to the left. In the subsequent phase synchronous rectification the difference between the areas above and below the curve to the right and left, respectively, of the zero point will appear in the form of a voltage which is integrated across the low pass filter 15. In case of a resistance as low as 100 kohm, the voltage will attain a constantly low value because the current is not able to make the voltage increase further across the measurement capacitor.

Figure 6:
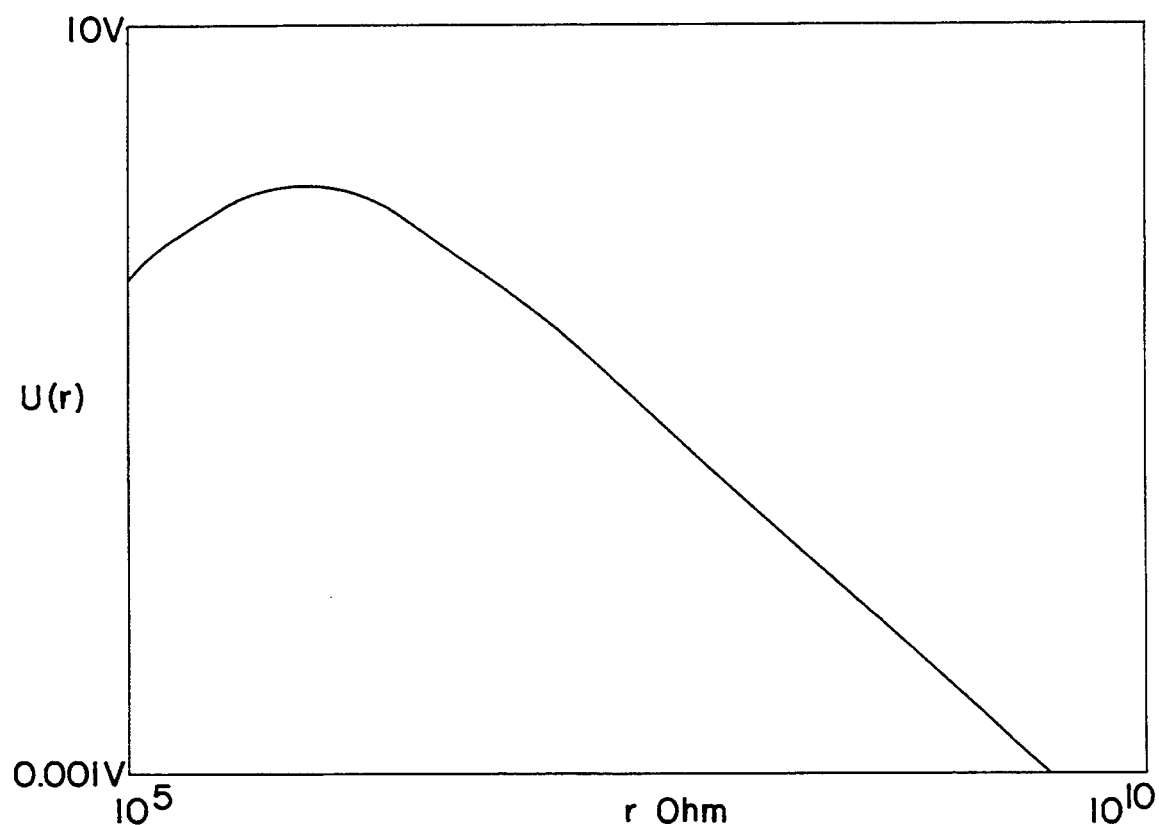

The curve shown in FIG. 6 represents the voltage immediately after the phase synchronous rectifier 6 as a function of the resistive loss in the measurement capacitor. The curve shows the theoretical calculation on a mathematical model of the circuit based on the following integral:

$$U(r) = \int_0^{100 \cdot 10^{-6}} \frac{1}{100 \cdot 10^{-6}} \left( i \cdot r - i \cdot r \cdot e^{\frac{-t}{rc}} - \frac{i \cdot r \cdot e^{\frac{-100 \cdot 10^{-6}}{rc}}}{2} \right) dt$$

wherein the following figures and values are used in the example:
constantly supplied current $i = 10 \times 10^{-6}$ A,
equivalent loss resistance in measurement capacitor $r = 10^5 - 10^{10}$ ohm,
integration time $t = 0 - 100 \times 10^{-6}$ s,
capacity of measurement capacitor $c = 50 \times 10^{-12}$ F.

In order to ensure a correct detection of the resistive loss in the measurement capacitor and hence of the humidity content in the refrigerant, the measuring range should preferably be selected so that the voltage is registered on the linear piece of the curve in FIG. 6, i.e., at loss resistances of more than 2-3 Mohm in the example shown.

It is noted that the circuit described above is designed to operate with absolute values in the registration of the resistive loss in the measurement capacitor. This is not the case in, e.g., the above mentioned GB patent application No. 2,045,442A, where the result is provided as a relative quantity. Thus, by means of the invention a certainty as to the long-time stability of the circuit is obtained so that an ageing and hence a change in the values of the components do not result in a shift of the measuring range. At the same time, this means that calibration of the circuit and the measurement capacitor during production can be effected by a separate test. Thus, it is not necessary to calibrate the measurement capacitor and the circuit together, nor is it necessary to effect a later adjustment, which is often the case with other types of devices.

We claim:

1. In an apparatus for the registration of the humidity and acid content of a refrigerant or of another non-polar liquid, the apparatus comprising a capacitive sensing element for placing in contact with the refrigerant or liquid, said sensing element having electrodes consisting of two different metals with different normal potentials, and in which apparatus the determination of humidity is carried out by measuring a resistive loss in the sensing element, the improvement including A.C. voltage source means connected to said sensing element, and an electrical circuit connected to said sensing element, said electrical circuit comprising means for converting the resistive A.C. loss in the capacitive sensing element to an absolute D.C. voltage when measuring humidity and means for determining the absolute D.C. current delivered by the sensing element when measuring acid.

2. An apparatus according to claim 1, wherein the electrodes of the capacitive sensing element are designed as two mutually engaging cam-shaped plates.

3. An apparatus according to claim 1, wherein the electrodes are in the form of coatings on a printed circuit board.

4. An apparatus according to claim 1, wherein the electrodes consist of Cu and another metal selected from the group consisting of Ni and Al.

5. An apparatus according to claim 1, wherein the electrical circuit on an output is connected to a relay, and the circuit is adapted to trip the relay upon exceeding a predetermined threshold value.

6. An apparatus according to claim 1, wherein said means for converting the resistive A.C. loss in the capacitive sensing element to an absolute D.C. voltage comprises an integrator of which the capacitive sensing element forms part, a phase synchronous rectifier connected to the integrator and a humidity detector circuit connected to the rectifier.

7. An apparatus according to claim 6, wherein the integrator comprises an operational amplifier having an input and an output, and wherein said capacitive element is connected to both said input and said output.

8. An apparatus according to claim 6, wherein the means for determining the D.C. current delivered by the capacitive sensing element comprising a voltage divider connected across the sensing element and an acid detector circuit connected to said voltage divider.

9. An apparatus according to claim 6 wherein the A.C. voltage source means is a square-wave oscillator.

* * * * *

UNITED STATES PATENT AND TRADEMARK OFFICE
CERTIFICATE OF CORRECTION

PATENT NO. : 5,439,644
DATED : August 8, 1995
INVENTOR(S) : Asger GRAMKOW et al.

It is certified that error appears in the above-indentified patent and that said Letters Patent is hereby corrected as shown below:

On title page, change the following, item

[86]  PCT No.: PCT/DK92/00189

Signed and Sealed this

Tenth Day of October, 1995

*Attest:*

BRUCE LEHMAN

*Attesting Officer*      *Commissioner of Patents and Trademarks*